United States Patent
Peters

(10) Patent No.: US 9,314,203 B2
(45) Date of Patent: Apr. 19, 2016

(54) SENSOR FOR FOETAL MONITORING

(71) Applicant: Christian Hendrik Leonard Peters, Rosmalen (NL)

(72) Inventor: Christian Hendrik Leonard Peters, Rosmalen (NL)

(73) Assignee: Nemo Healthcare B.V., Eindhoven (NL)

(*) Notice: Subject to any disclaimer, the term of this patent is extended or adjusted under 35 U.S.C. 154(b) by 0 days.

(21) Appl. No.: 14/054,091

(22) Filed: Oct. 15, 2013

(65) Prior Publication Data

US 2015/0105646 A1  Apr. 16, 2015

(51) Int. Cl.
  *A61B 5/0448* (2006.01)
  *A61B 5/00* (2006.01)
  *A61B 5/0492* (2006.01)

(52) U.S. Cl.
  CPC ............ *A61B 5/4343* (2013.01); *A61B 5/0448* (2013.01); *A61B 5/0492* (2013.01); *A61B 5/4325* (2013.01)

(58) Field of Classification Search
  CPC . A61B 5/0444; A61B 5/0448; A61B 2503/02
  USPC .................................................. 600/382, 511
  See application file for complete search history.

(56) References Cited

U.S. PATENT DOCUMENTS

| | | | |
|---|---|---|---|
| 3,380,445 A | 4/1968 | Frasier | |
| 3,565,060 A * | 2/1971 | Sipple | 600/508 |
| 3,703,168 A * | 11/1972 | Frink | 600/511 |
| 4,256,118 A | 3/1981 | Nagel | |
| 4,742,828 A | 5/1988 | Sundstrom | |
| 4,884,885 A | 12/1989 | Schweinsberg | |
| 5,125,405 A | 6/1992 | Schmid | |
| 5,197,472 A * | 3/1993 | DiSabito | 600/391 |
| 5,402,780 A * | 4/1995 | Faasse, Jr. | 600/392 |
| 6,421,558 B1 | 7/2002 | Huey et al. | |
| 6,816,744 B2 | 11/2004 | Garfield et al. | |
| 6,865,409 B2 * | 3/2005 | Getsla et al. | 600/393 |
| 7,206,630 B1 * | 4/2007 | Tarler | 600/509 |
| 7,333,850 B2 | 2/2008 | Marossero et al. | |
| 7,925,323 B2 * | 4/2011 | Meyer | 600/382 |
| 8,750,958 B2 * | 6/2014 | Storm | 600/384 |
| 2005/0154438 A1 * | 7/2005 | Fuller et al. | 607/148 |
| 2007/0191728 A1 | 8/2007 | Shennib | |
| 2011/0112440 A1 * | 5/2011 | Euliano et al. | 600/588 |

(Continued)

FOREIGN PATENT DOCUMENTS

DE  19809930 A1  9/1999
EP  0274577 A1  7/1988

(Continued)

OTHER PUBLICATIONS

European Search Report; Mailed Jan. 29, 2015 for corresponding EP Application No. 14188880.0.

(Continued)

*Primary Examiner* — Lee S Cohen
(74) *Attorney, Agent, or Firm* — Mendelsohn Dunleavy, P.C.

(57) ABSTRACT

A sensor for foetal monitoring, in particular for measuring electrophysiological signals, e.g. electrical activity of the uterus of a pregnant woman and/or of the heart of a foetus. The sensor includes a plurality of signal electrodes and a ground electrode mounted in or on a substrate, and a connector for connecting the sensor to a monitoring system. The ground electrode is positioned about or between a pair of signal electrodes.

31 Claims, 2 Drawing Sheets

(56) References Cited

U.S. PATENT DOCUMENTS

| | | |
|---|---|---|
| 2011/0196220 A1 | 8/2011 | Storm |
| 2012/0150010 A1 | 6/2012 | Hayes-Gill et al. |
| 2013/0018249 A1 | 1/2013 | Storm |
| 2014/0180169 A1 | 6/2014 | Peters et al. |

FOREIGN PATENT DOCUMENTS

| | | |
|---|---|---|
| JP | H08299294 A | 11/1996 |
| JP | 2012183082 A | 9/2012 |
| WO | WO02096288 A1 | 12/2002 |
| WO | WO2007095457 A2 | 8/2007 |
| WO | WO2013130979 A1 | 9/2013 |

OTHER PUBLICATIONS

Rabotti, Chiara, et al. "Estimation of internal uterine pressure by joint amplitude and frequency analysis of electrohysterographic signals." Physiological Measurement 29.7 (2008): 829-841.

Rabotti, Chiara, et al. "Relationship between electrohysterogram and internal uterine pressure: a preliminary study." Engineering in Medicine and Biology Society, 2006. EMBS'06. 28th Annual International Conference of the IEEE. IEEE, 2006, pp. 1661-1664.

Devedeux, Dominique, et al. "Uterine electromyography: a critical review." American journal of obstetrics and gynecology 169.6 (1993): 1636-1653.

\* cited by examiner

SENSOR FOR FOETAL MONITORING

BACKGROUND OF THE INVENTION

1. Field of the Invention

The invention relates to a sensor for foetal monitoring, in particular for measuring electrophysiological signals, e.g. electrical activity of the uterus of a pregnant woman and/or of the heart of a foetus, comprising a plurality of signal electrodes and a ground electrode mounted in or on a substrate, and a connector for connecting the sensor to a monitoring system.

2. Description of the Related Art

US 2012/0150010 relates to an apparatus and method for detecting uterine activity using cutaneous electrodes on the maternal abdomen to obtain electrophysiological signals that can be used to obtain foetal and maternal heart rate. The apparatus includes a first input for receiving electrical signals from the cutaneous electrodes and a second input for receiving movement signals indicative of a movement of the maternal body from a movement detector. A signal processor separates a uterine electromyogram signal from foetal and maternal heart rate signals and filters out motion artefacts from the electromyogram using the movement signals. An output presents electrohysterogram (EHG) data from the uterine electromyogram signal.

WO 2013/130979 relates to foetal monitoring and, more particularly, to an electronic external foetal monitoring system that includes a self adhering single use dermal patch including embedded sensors that can be attached to the skin of an expectant maternal patient and is configured to record foetal heart rate, uterine activity, and uterine integrity.

WO 2007/095457 relates to an integrated patch for the non-invasive monitoring of a laboring woman. The patch incorporates biopotential electrodes for sensing foetal ECG and EMG indicative of myometrial activity. The patch also incorporates a processor for extracting labor activity and foetal heart activity after filtering out maternal ECG from the composite biopotential signal present on the abdomen of the pregnant woman.

It is an object of the present invention to provide an improved sensor.

SUMMARY OF THE INVENTION

To this end, the sensor according to the invention is characterized in that the ground electrode is positioned about, e.g. annularly about, or between a pair of signal electrodes. In an embodiment, the centers of the ground electrode and the centers of the pair of signal electrodes are positioned on an imaginary line.

The present invention enables accurate measurements and yet a compact design of the sensor that, in principle, requires no or little bending of the sensor when placing it on a patient. Thus, establishing efficacious electrical contact between the skin of a patient and the ground electrode is relatively simple.

In an embodiment, the signal electrodes and ground electrode are symmetrical about an imaginary line perpendicular to an imaginary line through the centers of the electrodes and/or symmetrical about an imaginary line through the centers of the electrodes.

Thus, the sensor can be oriented with either of the signal electrodes up and/or the connector can be oriented to either side of the abdomen of a pregnant woman e.g. to suit the location of a monitoring system. In a refinement, the connector extends at an angle α to an imaginary line through the centers of the electrodes, wherein α is in a range from 70 to 110°, preferably in a range from 80 to 100°, preferably about 90°.

In further embodiment, the center to center distance of the signal electrodes in the pair is in a range from 70 to 110 mm, preferably in a range from 80 to 100 mm, preferably in a range from 85 to 95 mm, and/or the signal electrodes have an effective diameter in a range from 25 to 40 mm, preferably in a range from 28 to 37 mm, preferably in a range from 30 to 35 mm, and/or the surface area of the ground electrode is at least twice the surface area of at least one, preferably each of the signal electrodes, e.g. substantially equal to or larger than the combined surface area of the pair of signal electrodes. Electrodes in these ranges were found to provide improved signal to noise ratio.

In a further embodiment, the ground electrode has an effective diameter in a range from 30 to 60 mm, preferably in a range from 35 to 55 mm, preferably in a range from 30 to 50 mm. Employing a ground electrode in this range was found to reduce effects resulting from movements of the patient and increase reliability of the measurements.

In another embodiment, the sensor is disposable, i.e. is intended for single use.

In a further embodiment, the sensor comprises a memory, e.g. and (E)EPROM on a printed circuit board, that is accessible via the connector. The memory can be employed to store information that e.g. enables verifying the authenticity and/or shelf life of the sensor and/or previous use, e.g. to prevent re-use, and can be employed to link the sensor to a specific patient or register parameters relating to the use of the sensor, such as duration of use.

In a particularly compact yet efficacious embodiment, the sensor has a ground electrode and precisely two signal electrodes, i.e. three electrodes in all.

The invention further relates to a system for processing electrophysiological signals, in particular electrophysiological signals, e.g. electrical activity of the uterus of a pregnant woman and/or of the heart of a foetus, comprising a processing unit, optionally a presentation device, and a sensor according to the present invention. In an embodiment, the system comprises an input for receiving, via the sensor, an electrophysiological signal that is measured on the abdomen of a pregnant woman, a filter for receiving the electrophysiological signal and for providing a filtered electrohysterogram signal, the filter being configured to allow passage of frequencies of the electrophysiological signal in a range from 0 Hz to 3 Hz and to attenuate frequencies outside this range. The system further comprises a window function applicator for receiving the filtered electrohysterogram signal and for providing an output waveform. The window function applicator is configured to generate the output waveform by continuously applying a window function to samples of the filtered electrohysterogram signal, wherein a single application of the window function comprises adding, according to the window function, samples of the filtered electrohysterogram signal of an interval of time preceding the application of the window function, and an output for providing the output waveform, the output waveform simulating output data of a tocodynamometer or an intra-uterine pressure catheter, the output data representing data relating to uterine contractions.

Further details of a suitable system can be found in U.S. patent application Ser. No. 13/726,293 "Electrophysiological monitoring of uterine contractions" and corresponding European patent application 12199341.4, which are incorporated herein by reference.

The present invention also relates to a method of foetal monitoring by measuring electrophysiological signals, e.g.

electrical activity of the uterus of a pregnant woman and/or of the heart of a foetus, comprising the steps of preparing a sensor placement site at the abdomen of a pregnant woman and placing, at that site, a sensor according to the present invention. In an embodiment, the sensor placement site is prepared by means of an abrasive, e.g. an abrasive gel, preferably an abrasive tape. The combination of preparing a sensor site with abrasive tape and the sensor according to the present invention appeared to result in particularly straightforward placement and reliable measurements.

Within the framework of the present invention, the term "effective diameter" of an electrode is defined as the diameter of an imaginary circular disc having the same surface area as that electrode. If, e.g., the electrode is circular, the effective diameter is equal to the actual diameter.

The invention will now be explained in more detail with reference to the Figures, which show a preferred embodiment of the present sensor.

DETAILED DESCRIPTION OF THE INVENTION

It is noted that the Figures are schematic in nature and that details, which are not necessary for understanding the present invention, may have been omitted. Identical element and elements performing an at least substantially identical function have been indicated the same numeral.

Figure 1:
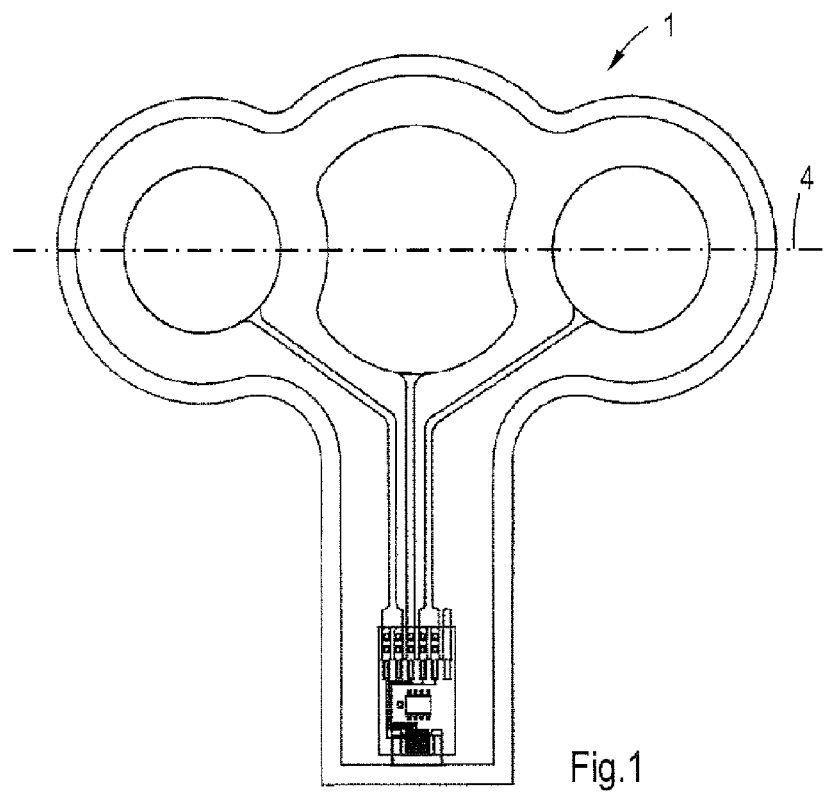
FIG. 1 is a top view of a sensor according to the present invention.
Figure 3:
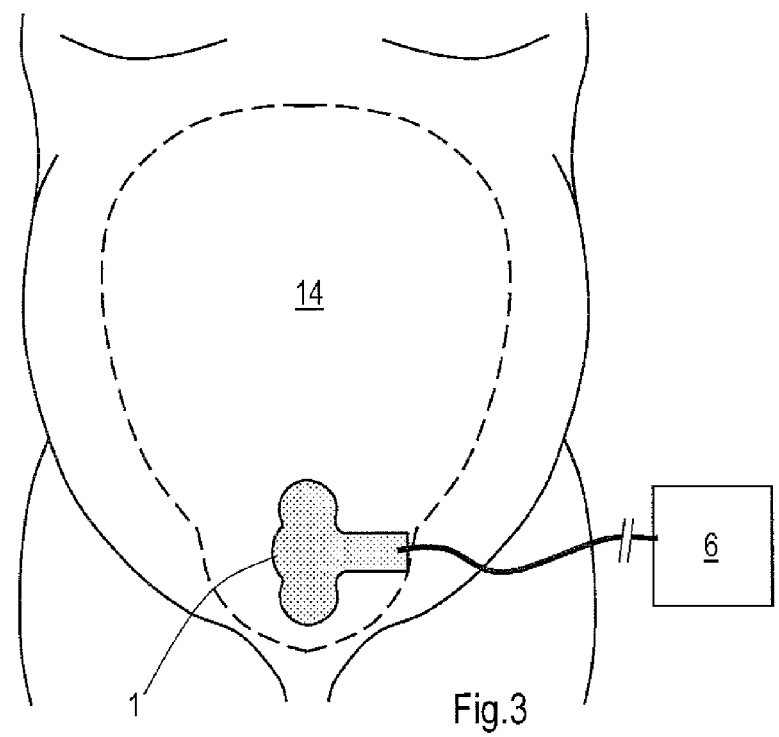
FIG. 3 shows a system for processing electrophysiological signals comprising a sensor as shown in FIGS. 1 and 2 placed on the abdomen of a pregnant woman.
Figure 2:
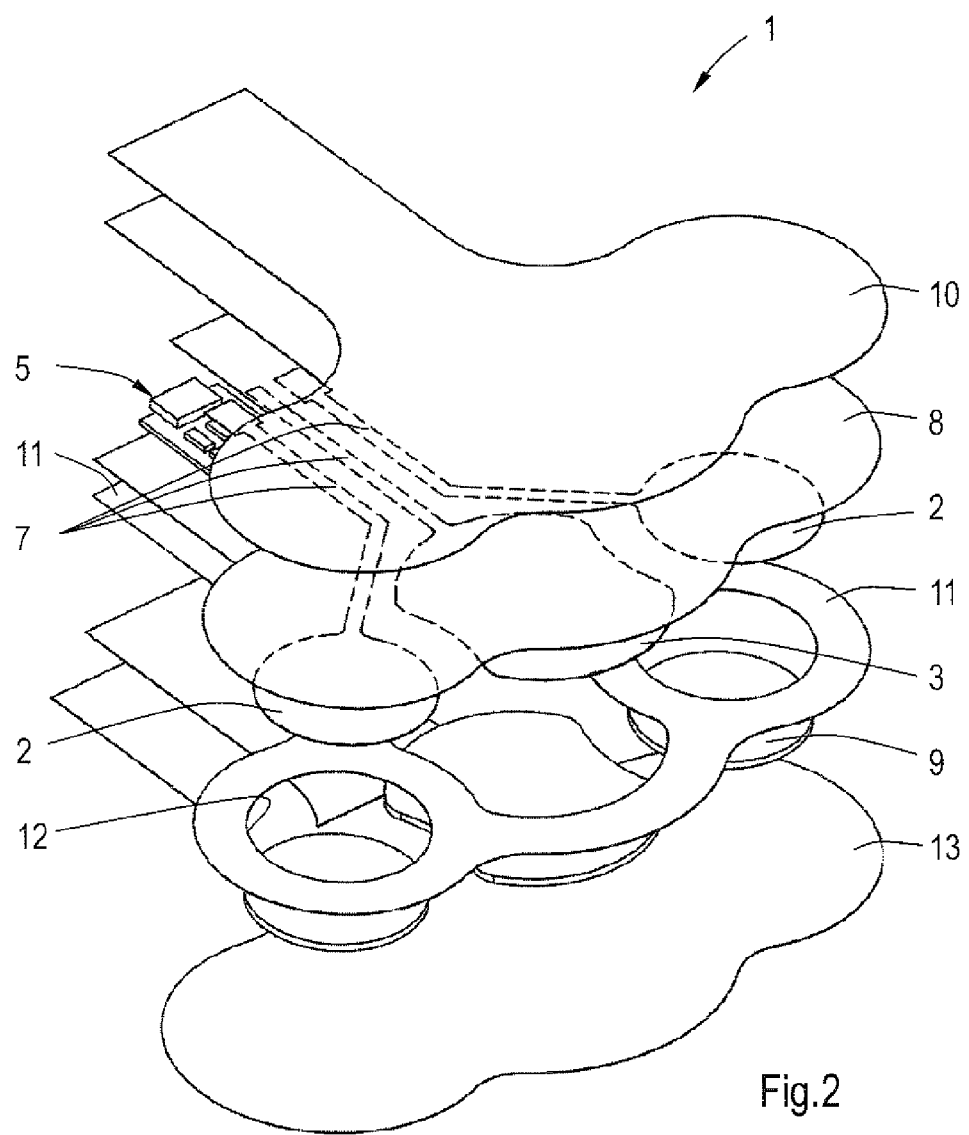
FIG. 2 is an exploded view of the sensor shown in FIG. 1.

FIGS. 1 to 3 show a sensor for foetal monitoring, in particular measuring electrophysiological signals, e.g. electrical activity of the uterus of a pregnant woman and/or of the heart of a foetus, comprising a pair of cutaneous and/or capacitive signal electrodes 2 and a cutaneous and/or capacitive ground electrode 3. In this example, the signal electrodes are circular and are located at a center to center distance of 90 mm. Seen in top view, the ground electrode is positioned between the signal electrodes has a surface area that is twice the surface area of each of the signal electrodes. The ground electrode is also circular with two recesses on opposite sides to provide sufficient distance, e.g. from 7 to 15 mm, and thus isolation between the ground electrode and the signal electrodes. The center of the ground electrode 3 and the centers of the pair of signal electrodes 2 are positioned on an imaginary line 4. The sensor further comprises a connector 5 for connecting the sensor 1 to a monitoring system 6, as shown in FIG. 3. The electrodes 2, 3 are electrically connected to the connector 5 by means of wires or leads 7 made from an electrically conducting material.

In this example, the electrodes 2, 3 and leads 7 are made of a foil or film of a conducting material, e.g. a film of Ag/AgCl (silver/silver chloride), that is adhered to or deposited on a substrate, e.g. a polyester sheet 8. The electrodes 2, 3 in turn are covered by a further conductive material, e.g. an adhesive hydrogel 9.

In this example, to protect the electrodes and the leads and to facilitate handling, a foam or nonwoven layer 10, 11 is adhered to both sides of the substrate 8. The foam or nonwoven layer 11 on the side of the substrate where the electrodes 2, 3 are located comprises openings 12 which correspond in shape, size and position to the electrodes. The hydrogel 9 is located in these openings. Further, the foam or nonwoven layer 11 is provided with additional adhesive in the areas surround the hydrogel. A protective foil 13 is adhered to the sensor and the sensor is stored in a sterile package (not shown).

During use, shown in FIG. 3, the sensor 1 is removed from its package and the protective foil 13 removed. A sensor placement site is prepared, by means of abrasive tape, at the abdomen of a pregnant woman 14. The sensor is placed at that site and connected to a monitoring system, which is no ready for foetal monitoring.

Particular embodiments of the invention are as follows. In a first embodiment, the invention relates to a sensor for foetal monitoring, in particular for measuring electrophysiological signals, e.g. electrical activity of the uterus of a pregnant woman and/or of the heart of a foetus, comprising a plurality of signal electrodes and a ground electrode mounted in or on a substrate, and a connector for connecting the sensor to a monitoring system, characterized in that the ground electrode is positioned about or between a pair of signal electrodes.

In a second embodiment, the sensor according to the first embodiment has the centers of the ground electrode and the centers of the pair of signal electrodes positioned on an imaginary line.

In a third embodiment, the sensor according to the second embodiment has the signal electrodes and ground electrode located symmetrically about an imaginary line perpendicular to an imaginary line through the centers of the electrodes and/or symmetrical about an imaginary line through the centers of the electrodes.

In a fourth set of embodiments, in the sensor according to any one of the preceding embodiments the connector extends at an angle α to an imaginary line through the centers of the electrodes, wherein a is in a range from 70 to 110°, preferably in a range from 80 to 100°, preferably about 90°.

In a fifth set of embodiments, in the sensor according to any one of the preceding embodiments, the center to center distance of the signal electrodes in the pair is in a range from 70 to 110 mm, preferably in a range from 80 to 100 mm, preferably in a range from 85 to 95 mm.

In a sixth set of embodiments, in the sensor according to any one of the preceding embodiments, the signal electrodes have an effective diameter in a range from 25 to 40 mm, preferably in a range from 28 to 37 mm, preferably in a range from 30 to 35 mm.

In a seventh set of embodiments, in the sensor according to any one of the preceding embodiments, the surface area of the ground electrode is at least twice the surface area of at least one, preferably both or all of the signal electrodes.

In an eighth set of embodiments, in the sensor according to any one of the preceding embodiments, the ground electrode has an effective diameter in a range from 30 to 60 mm, preferably in a range from 35 to 55 mm, preferably in a range from 30 to 50 mm.

In a ninth set of embodiments, in the sensor according to any one of the preceding embodiments, the sensor is disposable.

In a tenth set of embodiments, the sensor according to any one of the preceding embodiments, includes a memory that is accessible via the connector.

In an eleventh set of embodiments, the sensor according to any one of the preceding embodiments has a ground electrode and precisely two signal electrodes, i.e. three electrodes in all.

In a twelfth set of embodiments, in the sensor according to any one of the preceding embodiments, the signal electrodes are circular and the ground electrode is substantially circular with recesses on opposite sides to provide sufficient isolation between the ground electrode and the signal electrodes.

In yet another set of embodiments, the invention is a system for processing electrophysiological signals, in particular electrophysiological signals, e.g. electrical activity of the uterus of a pregnant woman and/or of the heart of a foetus, comprising a processing unit, optionally a presentation device, and a sensor according to any one of the preceding embodiments.

In yet another set of embodiments, the invention relates to a method of foetal monitoring by measuring electrophysiological signals, e.g. electrical activity of the uterus of a pregnant woman and/or of the heart of a foetus, including the steps of preparing a sensor placement site at the abdomen of a pregnant woman and placing, at that site, a sensor according to any one of the preceding embodiments or employing a system according to any one of the preceding embodiments.

In a further set of embodiments, in the method according to any previous embodiment the sensor placement site is prepared by means of an abrasive, preferably abrasive tape.

The invention is not restricted to the embodiments described above and can be varied in numerous ways within the scope of the claims. For instance, instead of being positioned between the signal electrodes, the ground electrode can be at least substantially annular or shaped as a lemniscate and positioned about the signal electrodes.

The invention claimed is:

1. A sensor for foetal monitoring comprising:
   a substrate,
   a plurality of signal electrodes mounted in or on the substrate, each said signal electrode having an effective diameter of at least 25 mm,
   a ground electrode mounted in or on the substrate and positioned about or between a pair of the signal electrodes, and
   a connector configured for connecting the signal electrodes of the sensor to a monitoring system.

2. The sensor for foetal monitoring according to claim 1, wherein the sensor is configured for measuring electrophysio logical signals.

3. The sensor for foetal monitoring according to claim 2, wherein the sensor is further configured for measuring electrical activity of a uterus of a pregnant woman and/or of a heart of a foetus.

4. The sensor according to claim 2, wherein a center of the ground electrode and centers of the pair of signal electrodes are positioned on an imaginary line.

5. The sensor according to claim 4, wherein the signal electrodes and the ground electrode are symmetrical about an imaginary line perpendicular to an imaginary line through the centers of the pair of signal electrodes and the center of the ground electrode and/or symmetrical about an imaginary line through the centers of the pair of signal electrodes and the center of the ground electrode.

6. The sensor according to claim 2, wherein the connector extends at an angle α to an imaginary line through centers of the pair of the signal electrodes and a center of the ground electrode, and wherein the angle α is in a range of from 70° to 110°.

7. The sensor according to claim 6, wherein the angle α is in a range of from 80° to 100°.

8. The sensor according to claim 6, wherein the angle α is about 90°.

9. The sensor according to claim 2, wherein a distance from a center of a first of the pair of the signal electrodes to a center of second of the pair signal electrodes is in a range of from 70 to 110 mm.

10. The sensor according to claim 9, wherein the distance is in a range of from 80 to 100 mm.

11. The sensor according to claim 9, wherein the distance is in a range of from 85 to 95 mm.

12. The sensor according to claim 2, wherein the signal electrodes have an effective diameter in a range of from 25 to 40 mm.

13. The sensor according to claim 2, wherein the signal electrodes have an effective diameter in a range of from 28 to 37 mm.

14. The sensor according to claim 2, wherein the signal electrodes have an effective diameter in a range of from 30 to 35 mm.

15. The sensor according to claim 2, wherein a surface area of the ground electrode is at least twice a surface area of at least one of the signal electrodes.

16. The sensor according to claim 2, wherein a surface area of the ground electrode is at least twice a combined surface area of at least two of the signal electrodes.

17. The sensor according to claim 2, wherein a surface area of the ground electrode is at least twice a combined surface area of all of the signal electrodes.

18. The sensor according to claim 2, wherein the ground electrode has an effective diameter in a range of from 30 to 60 mm.

19. The sensor according to claim 2, wherein the ground electrode has an effective diameter in a range of from 35 to 55 mm.

20. The sensor according to claim 2, wherein the ground electrode has an effective diameter in a range of from 30 to 50 mm.

21. The sensor according to claim 2, wherein the sensor is disposable.

22. The sensor according to claim 2, further comprising a memory that is connected to the connector so as to be accessible via the connector.

23. The sensor according to claim 2, having exactly one ground electrode and exactly two signal electrodes.

24. The sensor according to claim 2, wherein the signal electrodes are circular and the ground electrode is between the pair of signal electrodes, the ground electrode is substantially circular and the ground electrode is provided with recesses on opposite sides of the ground electrode to provide sufficient isolation between the ground electrode and the signal electrodes.

25. A system for processing electrophysiological signals comprising:
   a sensor according to claim 2 and
   a processing unit operatively associated with said sensor for receiving and processing signals from said sensor.

26. A system according to claim 25, further comprising a presentation device operatively associated with the processing unit for presenting output from said processing unit.

27. A system according to claim 25, wherein said electrophysiological signals are electrical activity of a uterus of a pregnant woman and/or of a heart of a foetus.

28. A method of foetal monitoring by measuring electrophysiological signals comprising steps of:
   preparing a sensor placement site at an abdomen of a pregnant woman, and
   placing, at said sensor placement site, a sensor according to claim 2.

29. The method according to claim 28, wherein the electrophysiological signals are electrical activity of the uterus of a pregnant woman and/or of a heart of a foetus.

30. The method according to claim 28, wherein the sensor placement site is prepared by means of an abrasive.

31. The method according to claim 30, wherein the abrasive is an abrasive tape.

* * * * *